Figure 1:
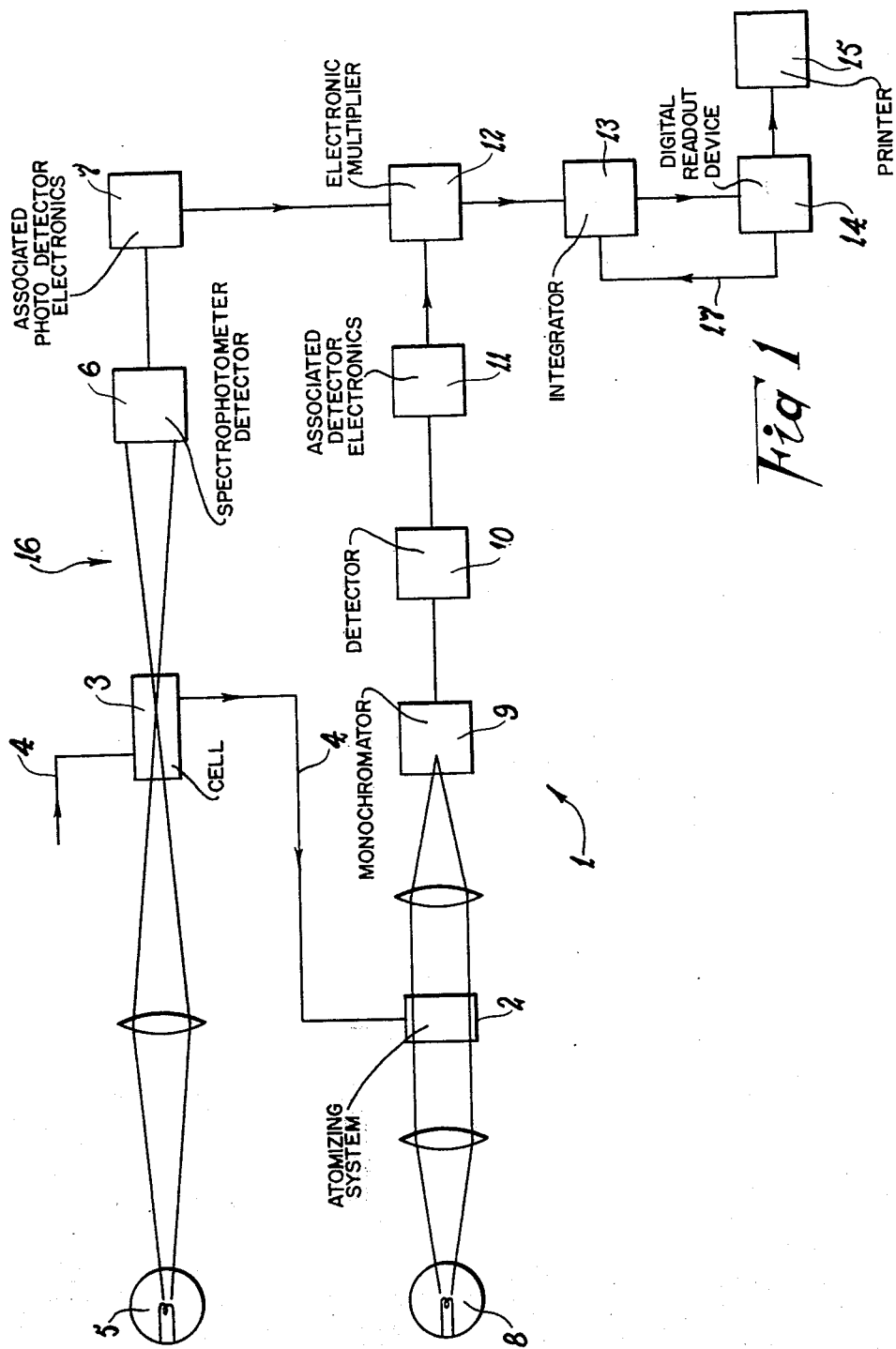

United States Patent [19]
Baird et al.

[11] 3,954,336
[45] May 4, 1976

[54] CHEMICAL ANALYSIS METHOD AND APPARATUS

[75] Inventors: Graeme Alexander Baird, Erskineville; Nicholas James Marshall, Gymea, both of Australia

[73] Assignee: Australian Selection, Sydney, Australia

[22] Filed: Oct. 23, 1973

[21] Appl. No.: 408,450

[30] Foreign Application Priority Data
Oct. 27, 1972 Australia.............................. 1003/72

[52] U.S. Cl.................................. 356/36; 356/73; 356/87
[51] Int. Cl.² ........................................ G01N 1/00
[58] Field of Search ................... 356/36, 72, 73, 87, 356/96

[56] References Cited
UNITED STATES PATENTS
2,811,891   11/1957   Roddy.............................. 356/36 X OTHER PUBLICATIONS
Yoe, Photometric Chemical Analysis, Vol. 1, John Wiley & Sons, Inc., New York, 1928, pp. 412–414.

Primary Examiner—Alfred E. Smith
Assistant Examiner—Matthew W. Koren
Attorney, Agent, or Firm—Lerner, David, Littenberg & Samuel

[57] ABSTRACT

A method of chemical analysis of a sample in solution in which the optical density of the solution is modified by addition of a dye to the solution, and the modified optical density is utilized in determining the concentration of the sample in the solution. That determination is effected by measuring the optical density of the dyed solution and applying a value thereto, and then comparing that value with a predetermined value which corresponds to a particular sample concentration. The actual sample concentration is assigned a value in accordance with the results of that comparison, and that assigned value is employed in determining the concentration of a particular element in the sample by spectral analysis. Apparatus for carrying out the method includes a first spectrophotometer for determining the optical density of the sample solution, and a second spectrophotometer for applying a value to the concentration of the element of interest in the atomized sample. The two spectrophotometers are connected through correction means whereby the element concentration value is corrected in accordance with the variations between the measured optical density value and the predetermined optical density value.

12 Claims, 2 Drawing Figures

CHEMICAL ANALYSIS METHOD AND APPARATUS

This invention relates to a method and apparatus for use in spectrum analysis, and is particularly although not exclusively concerned with the analysis of chemicals by the technique of flame spectroscopy. It will be convenient to hereinafter describe the invention in relation to flame spectroscopy, and the expression "flame spectroscopy" is to be understood as embracing atomic absorption, atomic fluorescence, and flame emission spectroscopy. The invention also relates to a method of preparing a sample to be used in spectrum analysis.

In conventional flame spectroscopy, the element to be determined is contained in a dilute solution which is sprayed into a flame located in the optical path of a spectrophotometer. If a sample containing the element of interest is initially provided in solid form, that sample must be dissolved and embodied in a solution to enable the subsequent analysis to be carried out. If the sample is initially in solution form, it may be nevertheless necessary to dilute that solution before analysis. In either case, the initial weight of the sample — i.e., solid or solution — must be accurately determined before the final dilute solution is prepared. The degree of dilution required in any particular case will be generally determined by reference to the initial concentration of the element in the sample and the sensitivity of the spectrophotometer.

It is also necessary to determine the precise weight of the final dilute solution, and as a matter of convenience that is usually a standard weight. The accuracy of the analysis will depend to a considerable degree upon the accuracy of the final solution weight, and consequently extreme care is required in measuring that solution, which measurement is performed manually using a balance instrument or finely calibrated glassware. During the actual analysis, the concentration of the element of interest in the atomized solution is determined, and that value is then related to the respective weights of the dilute solution and the initial sample, in order to calculate the concentration of the element in that sample.

A principal object of the present invention is to overcome the need for accurately determining the final weight or volume of the dilute solution, and therefore provide an improved method of spectrum analysis. In practice, it is generally acceptable to regard volume and weight as synonymous for dilute aqueous solutions having a density equalling 1 gram per cubic centimeter at 20° centigrade.

A further object of the invention is to provide a novel method of preparing a sample for spectrum analysis. Still another object of the invention is to provide a new and improved apparatus for performing spectrum analysis.

The primary distinguishing feature of a method according to the invention is that the optical density of the dilute solution is used as the basis for determining the sample diluent ratio, thereby avoiding the necessity to accurately measure the weight or volume of the final solution, although the initial weight of the sample must be known as with prior methods. The normal optical density of the dilute solution is modified by introduction of a measured quantity of a suitable dye into the solution, and that provides the basis for subsequent calculations as hereinafter described in detail.

It is to be understood that the word "dye" as used throughout this specification embraces all additives capable of altering the optical density of the solution — that is, altering the degree to which the solution is pervious to light radiation. Such an additive need not be a material normally recognized as a dye in the strict sense of the word.

The following description refers in more detail to these essential features and further optional features of the invention. To facilitate an understanding of the invention, reference is made to the accompanying drawings where these features are illustrated in preferred form. It is to be understood however, that the essential and optional features of the invention are not limited to the specific forms of these features as shown in the drawings.

Figure 2:
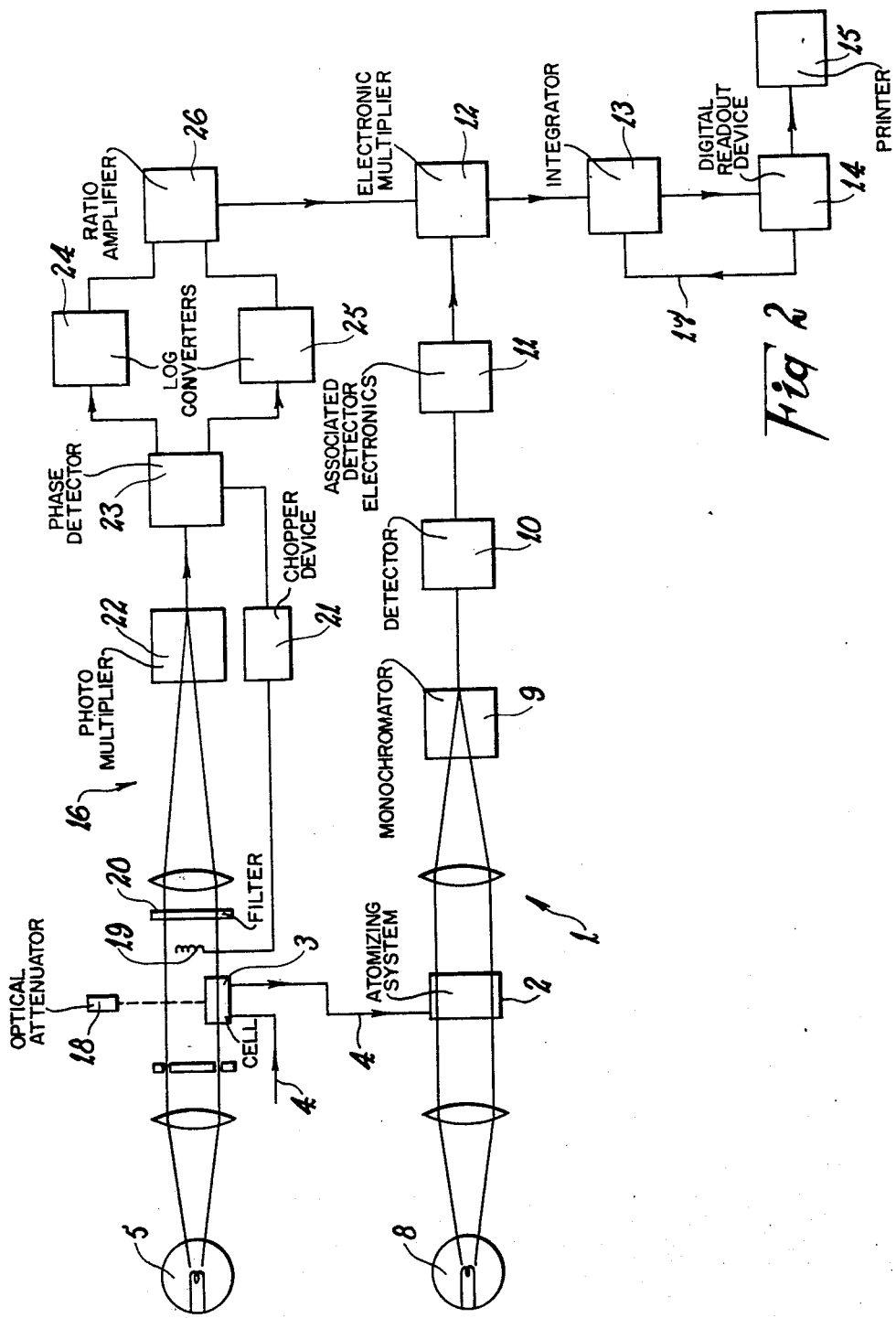

In the drawings:

FIG. 1 is a block diagram of one form of apparatus for use in performance of the invention; and FIG. 2 is a block diagram of an alternative form of apparatus for use in performance of the invention.

It will be understood from the foregoing passages, that preparation of a sample in accordance with the invention requires inclusion of a dye in the sample solution. Initially, the sample may be prepared as in the past — that is, it is dissolved if not already in solution, and the solution is diluted as may be necessary to arrive at a suitable concentration for use in the selected analysis technique. Contrary to prior methods however, the final weight or volume of the dilute solution need not be accurately determined, although it is necessary to know the approximate ratio of sample to diluent. A measured quantity of dye is then added to the dilute solution, and the resulting combination is mixed to obtain a substantially uniform final solution. For best results, an inert dye should be used, and that dye should have an absorption band at a wavelength which is completely removed from and independent of any absorption band wavelength of the sample and diluent.

In applying such a dyed sample to a method of spectrum analysis, the dye concentration of the solution is determined, and the sample is then analysed in the selected manner. The element concentration value determined by that analysis is related to the dye concentration value, and the resulting value is then compared with the corresponding value of a standard dye solution containing the element of interest. The concentration of the element in the initial sample can be calculated from that comparison.

Consider for example, a typical method according to the invention in which it is desired to determine the concentration of copper in a particular sample, and the selected technique of analysis can be satisfactorily performed with solution containing 100 parts of water or other diluent to 1 part of sample. Assuming the sample is initially in solid form, it is accurately weighed and then dissolved in acid. The sample solution is then diluted with water to achieve an approximate final sample concentration of 1 gram to 100 grams of water. It is not necessary however, that the ratio be accurately determined, nor is it necessary to determine the weight of the diluted solution. A predetermined quantity of dye, which is measured accurately, is then added to the solution and mixed as necessary to result in a uniform dye solution.

A standard dye solution may be prepared before or after preparation of the sample solution, and that standard includes a known quantity of the element of interest, which in this case is copper. For example, the standard may consist of an accurately prepared solution of 3 parts per million copper in 100 grams of water and 5 grams of the selected dye. That is, the same dye is used in both the standard and sample solutions, and the same quantity exists in both solutions. It is known that the standard solution contains 5 grams of dye in 100 grams of water, whereas in the sample solution there is 5 grams of dye and approximately 100 grams of water.

The optical density of the standard solution is determined, and it will be assumed that the density is measured at 0.5. That density is of course directly proportional to the concentration of dye in the solution, and that concentration is known from the initial measurements of the components of the solution. The standard solution is then analysed by the selected technique to determine a value corresponding to the concentration of the element in the solution, which concentration is also known.

It is then possible to accurately determine the element concentration of sample by measuring the optical density of the sample solution and subjecting that solution to the same form of spectrum analysis as employed in relation to the standard solution. The optical density of the sample solution is used as the basis for determining the sample-diluent ratio. That is if the ratio is greater than 1:100, the optical density can be expected to be less than 0.5 because the same quantity of dye is contained in both the standard and sample solutions. Thus, any difference between the respective optical densities is allowed for by suitable adjustment of the analysing apparatus — e.g. spectrophotometer — and the element concentration values of the two solutions can then be directly related to obtain a determination of the element concentration in the initial sample.

The invention is especially suitable for use with spectrophotometer apparatus as used in analysis by the atomic absorption and atomic fluorescence techniques. FIG. 1 is a schematic representation of one particular apparatus embodying the principles of the invention and in which an atomic absorption spectrophotometer 1 is employed to determine the concentration of the element of interest in the sample. In that apparatus, the sample solution is introduced into the atomizing system 2, which is usually a flame, by means of a venturi type nebuliser arranged to disperse a small percentage of the solution as a cloud of minute droplets in a known manner. According to the present invention, the apparatus includes a flow through cell 3 located in the sample feed line 4 before the nebuliser and being located in the light path of a spectrophotometer lamp 5. The arrangement is such that the sample solution passes through the cell 3 and its colour intensity (i.e., optical density) is sensed by a spectrophotometer detector 6 which has associated electronics 7 of a known kind operable to apply a value to the optical density of the sample solution. Obviously, other optical density measuring means may be employed, but a spectrophotometer is preferred, and in some cases that may be the same spectrophotometer as used to measure the element concentration.

The photo detector electronics 7 of the optical density spectrophotometer 16 may be preset to automatically compare the optical density value assigned to the sample with a value determined for the optical density of the standard solution, and produce a corrective signal which corresponds to the actual concentration of the sample in the solution. Alternatively, both the standard solution value and the sample solution value may be fed to appropriate electronics (not shown) which functions to provide a corrected value which takes the form of the output signal from the optical density spectrophotometer 16.

The element concentration spectrophotometer 1 shown in FIG. 1 is a standard atomic absorption type including a lamp 8 with associated lens system for concentrating a light beam through the atomizer system 2. A monochrometer 9 is provided for isolating the radiation of interest and passing that radiation to the detector 10 and associated electronics 11 which functions to apply a value to the concentration of the absorbing atoms within the atomized sample. All such components function in a known manner.

The element concentration spectrophotometer 1 is initially set to give a value for the element concentration in a solution having a particular standard optical density, which is directly proportional to the dye-diluent ratio. The optical density spectrophotometer 16 is connected to the spectrophotometer 1 through correction apparatus such that any variation from the standard optical density is relayed to the spectrophotometer 1 and that spectrophotometer is automatically adjusted so that it will give a substantially true element concentration reading for the sample under test. The correction apparatus may take any appropriate form, but in the embodiment of FIG. 1 includes an electronic multiplier 12 which is connected to the outputs from both the detector electronics 7 and 11 respectively, and the multiplier 12 is operable in a known manner to provide an output signal proportional to the relationship between the element concentration value and the optical density value as assigned by the spectrophotometers 1 and 16 respectively. In particular, that output signal corresponds to the actual concentration of the element of interest within the sample, because the value initially assigned to that concentration by the spectrophotometer 1 is corrected by the output signal of the spectrophotometer 16 which corresponds to the variation between the standard optical density value and the optical density value assigned to the sample under observation.

The output from the multiplier 12 is connected to a printer 15 through an integrator 13 and digital read out device 14, all of which function in a known manner to provide a record of the actual concentration of the element in the sample. A reset channel 17 is connected between the integrator 13 and read out device 14 in accordance with known circuitry of this kind.

FIG. 2 provides a schematic representation of apparatus similar to that shown in FIG. 1, but in which the optical density spectrophotometer 16 includes a double beam detector system. In that arrangement, the flow through cell 3 is provided within the lens system of the spectrophotometer together with an optical attenuator 18, chopper device 19 and filter 20, all of which are of known construction and operate in a known manner. A chopper drive 21 is connected between the chopper 19 and a phase detector 23 to operate in a known manner. The radiation emitted from the lens system is detected by a photo multiplier 22 which is connected in turn to the phase detector 23. The phase detector 23 has two output channels which include respective log converters 24 and 25, and both channels are connected to a ratio amplifier 26. The channel containing the log converter 24 is arranged to assign a value to the optical density of the solution under consideration and the channel containing the log converter 25 is arranged to assign a value to the optical density of the standard solution. Consequently, the output from the ratio amplifier 26 provides a corrected signal which corresponds to the actual optical density of the sample solution, and that output and the output from the detector electronics 11 are connected into a multiplier 12 and related circuitry which functions as in the previously described embodiment.

As previously mentioned, the spectrophotometer 1 need not be of the atomic absorption type, but may be an atomic fluorescence spectrophotometer or flame emission spectrophotometer. In either case persons skilled in the relevant art will understand how the apparatus of the invention can be arranged to achieve the desired result. That is, the apparatus requires a spectrophotometer or other device for assigning a value to the dilution of the sample in the solution and comparing that value with a preset value or standard solution value, and a spectrophotometer (which may be the same as or different to the sample dilution spectrophotometer) for assigning a value to the concentration of the element of interest in the sample. Appropriate electronics is then provided to correct the element concentration value as initially assigned by the spectrophotometer in accordance with a signal corresponding to the sample-diluent ratio as determined by relating the aforementioned values.

It will be appreciated that the apparatus for carrying out a method in accordance with this invention may take any one of several forms.

Finally, it is to be understood that various alterations, modifications and/or additions may be introduced into the constructions and arrangements of parts previously described without departing from the spirit or ambit of the invention as defined by the appended claims.

Having now described our invention, what we claim as new and desire to secure by Letters Patent is:

1. A method of chemical analysis of a sample which includes an element of interest, including the steps of;
    adding a measured quantity of a dye to a solution containing a known quantity of said sample;
    measuring the optical density of said dyed sample solution;
    comparing said optical density of the sample solution with the optical density of a standard solution having a known dye concentration, and thereby determining a value for the concentration of said sample in said sample solution;
    subjecting said sample solution to spectral analysis so as to determine a value for the concentration of said element in said sample solution; and
    relating said sample concentration value and said element concentration value so as to determine the concentration of said element in said sample.

2. A method according to claim 1, wherein the same dye is used in both the sample solution and the standard solution, and the same quantity of said dye is included in each said solution.

3. The method according to claim 2, wherein the measured quantity of dye added to said solution containing a known quantity of said sample is sufficient to produce a dyed sample solution having a dye concentration which now is approximately the same as the dye concentration in said standard dye solution.

4. The method according to claim 1, wherein the standard solution contains a known concentration of the element of interest, and including subjecting said standard solution to spectrum analysis to establish a value equivalent to the concentration of said element in said standard solution, and said value equivalent to the concentration of said element in said standard solution is used as an analogue for determining the concentration of said element in said sample solution.

5. A method of chemical analysis of a sample which includes an element of interest, including the steps of;
    adding a measured quantity of a dye to a solution containing a known quantity of said sample;
    measuring the optical density of said dyed sample solution and utilizing said measurement to determine a value for the concentration of said sample in said solution, by comparing the measured optical density of said sample solution with the optical density of a standard solution having a known concentration of said dye, and determining a value for the concentration of said sample in said sample solution from that comparison;
    subjecting said solution to spectral analysis so as to determine a value for the concentration of said element in said solution; and
    relating said sample concentration value and said element concentration value so as to determine the concentration of said element in said sample.

6. The method according to claim 5, wherein said measured optical density is compared electronically with the optical density of said standard solution, and a corrected signal resulting from that comparison is utilized in assigning a value for the concentration of said sample and said solution.

7. Chemical analysis apparatus including;
    a light source;
    means for atomizing a sample in solution and the path of said light source;
    spectrometer means operable to detect atoms of a particular element in said atomized sample and supply a value for the concentration of said atoms in said sample solution;
    means for measuring the optical density of said sample solution;
    means for comparing said optical density of said sample solution with the optical density of a standard solution; and
    correction means responsive to variation between the optical density of said sample solution and the optical density of said standard solution, said correction means operable to correct said atom concentration value in accordance with the degree of said variation.

8. Apparatus according to claim 7, wherein said optical density measuring means includes a flow-through cell and a spectrophotometer connected to said cell, said cell being located in a line through which said sample solution is fed to said atomizing means.

9. Apparatus according to claim 7, wherein nebulizing is provided to disperse a fine spray of said sample solution, and said atomizing means includes a burner which functions to atomize part of said spray.

10. Apparatus according to claim 7, wherein said spectrophotometer means comprises an atomic absorption spectrophotometer.

11. Apparatus according to claim 7, wherein said spectrophotmeter means comprises an atomic fluorescence spectrophotometer.

12. Apparatus according to claim 7, wherein said spectrophotometer means comprises a flame emission spectrophotometer.

* * * * *